(12) United States Patent
Park et al.

(10) Patent No.: US 9,849,190 B2
(45) Date of Patent: Dec. 26, 2017

(54) PEPTIDE HAVING CANCER SELECTIVE TRANSLOCATION FUNCTION AND USE THEREOF

(71) Applicants: SNU R&DB FOUNDATION, Seoul (KR); Nano Intelligent Biomedical Engineering Corporation Co. Ltd, Seoul (KR)

(72) Inventors: Yoon Jeong Park, Seoul (KR); Chong-Pyoung Chung, Seoul (KR); Jin Sook Suh, Seoul (KR); Yoon Jung Choi, Gyeonggi-do (KR)

(73) Assignees: SNU R&DB FOUNDATION, Seoul (KR); NANO INTELLIGENT BIOMEDICAL ENGINEERING CORPORATION CO, LTD., Seoul (KR)

( * ) Notice: Subject to any disclaimer, the term of this patent is extended or adjusted under 35 U.S.C. 154(b) by 0 days.

(21) Appl. No.: 15/234,396

(22) Filed: Aug. 11, 2016

(65) Prior Publication Data
US 2016/0367694 A1    Dec. 22, 2016

Related U.S. Application Data

(63) Continuation of application No. 14/395,807, filed as application No. PCT/KR2013/008324 on Sep. 16, 2013, now abandoned.

(30) Foreign Application Priority Data

Sep. 18, 2012  (KR) ........................ 10-2012-0103620

(51) Int. Cl.
| | |
|---|---|
| *A61K 38/00* | (2006.01) |
| *A61K 47/64* | (2017.01) |
| *C07K 14/47* | (2006.01) |
| *C07K 7/08* | (2006.01) |
| *C12Q 1/26* | (2006.01) |
| *C12Q 1/58* | (2006.01) |
| *C12Q 1/66* | (2006.01) |
| *A61K 47/48* | (2006.01) |
| *G01N 33/574* | (2006.01) |
| *A61K 31/704* | (2006.01) |
| *A61K 49/00* | (2006.01) |

(52) U.S. Cl.
CPC ...... *A61K 47/48246* (2013.01); *A61K 31/704* (2013.01); *A61K 47/64* (2017.08); *A61K 49/0056* (2013.01); *C07K 7/08* (2013.01); *C07K 14/47* (2013.01); *C12Q 1/26* (2013.01); *C12Q 1/58* (2013.01); *C12Q 1/66* (2013.01); *C12Y 301/13* (2013.01); *G01N 33/574* (2013.01); *A61K 38/00* (2013.01); *C07K 2319/10* (2013.01)

(58) Field of Classification Search
CPC .... A61K 31/704; A61K 38/00; A61K 38/465; A61K 47/48246; A61K 47/64; A61K 49/0056; C07K 14/47; C07K 2319/10; C07K 7/08; C12Q 1/26; C12Q 1/58; C12Q 1/66; C12Y 301/13; G01N 33/574
USPC ............... 530/300, 327; 514/19.3, 19.4, 21.5
See application file for complete search history.

(56) References Cited

U.S. PATENT DOCUMENTS

| | | |
|---|---|---|
| 5,595,756 A | 1/1997 | Bally et al. |
| 2007/0071677 A1 | 3/2007 | Park et al. |
| 2012/0053129 A1 | 3/2012 | Park et al. |
| 2013/0237484 A1 | 9/2013 | Chung et al. |
| 2015/0165060 A1 | 6/2015 | Park et al. |

FOREIGN PATENT DOCUMENTS

| | | |
|---|---|---|
| KR | 10-2010-0094622 A | 8/2010 |
| KR | 10-2012-0026408 A | 3/2012 |

OTHER PUBLICATIONS

Auerbach, Robert, et al., "Angiogenesis Assays: Problems and Pitfalls", "Cancer and Metastasis Reviews", 2000, pp. 167-172, vol. 19.
Elliott, G., et al., "Intercellular Trafficking and Protein Delivery by a Herpesvirus Structural Protein", "Cell", Jan. 24, 1997, pp. 223-233, vol. 88.
Fawell, S., et al., "Tat-mediated delivery of heterologous proteins into cells", "Proc. Natl. Acad. Sci. USA", Jan. 1994, pp. 664-668, vol. 91.
Gura, T., "Systems for Identifying New Drugs are Often Faulty", "Science", Nov. 7, 1997, pp. 1041-1042, vol. 278.
Jain, R., "Barriers to Drug Delivery in Solid Tumors", "Scientific American", Jul. 1994, pp. 58-65.
Laus, R., et al., "Enhanced major histocompatibility complex class I-dependent presentation of antigens modified with cationic and fusogenic peptides", "Nature Biotechnology", Dec. 2000, pp. 1269-1272, vol. 18.
Liang, J., et al., "Synthesis of Doxorubicin-Peptide Conjugate with Multidrug Resistant Tumor Cell Killing Activity", "Bioorganic & Medicinal Chemistry Letters", Sep. 15, 2005, pp. 5071-5075, vol. 15.
Moon, C., et al., "In Vitro Assessment of a Novel Polyrotaxane-Based Drug Delivery System Integrated with a Cell-Penetrating Peptide", "J Control Release", Dec. 4, 2007, pp. 4350, vol. 124, No. 1-2.
Neidle, S., Ed., "Cancer Drug Design and Discovery", 2008, pp. 427-431, Publisher: Elsevier/Academic Press.

(Continued)

*Primary Examiner* — Julie Ha
(74) *Attorney, Agent, or Firm* — Hultquist, PLLC; Steven J. Hultquist

(57) ABSTRACT

A method of treating breast cancer is described, in which a peptide having cancer selective translocation function-doxoribicin conjugate is administered. The conjugate includes doxorubicin chemically linked to the N-terminus or C-terminus of a VEGF-binding protein transduction domain (VPTD) peptide represented as SEQ ID NO: 1, wherein the VPTD peptide and doxorubicin are linked to each other by a disulfide bond, and wherein the VPTD peptide binds specifically to vascular endothelial growth factor (VEGF) in tumor cells or tumor tissues.

2 Claims, 4 Drawing Sheets

(56) References Cited

OTHER PUBLICATIONS

Park, Y., et al., "Low molecular weight protamine as an efficient and nontoxic gene carrier: in vitro study", "J. Gene Med.", Apr. 24, 2003, pp. 700-711, vol. 5.

Park, Y., et al., "Nontoxic membrane translocation peptide from protamine, low molecular weight protamine (LMWP), for enhanced intracellular protein delivery: in vitro and in vivo study", "The FASEB Journal", Jul. 20, 2005, pp. 1555-1557, vol. 19, No. 11.

Qi, L., et al., "Cell-Penetrating Magnetic Nanoparticles for Highly Efficient Delivery and Intracellular Imaging of siRNA", "Biomacromolecules", Aug. 22, 2012, pp. 2723-2730, vol. 13.

Schwarze, S., et al., "In vivo protein transduction: intracellular delivery of biologically active proteins, compounds and DNA", "Trends in Pharmacological Sciences", Feb. 2000, pp. 45-48, vol. 21.

Sporn, M., et al., "Chemoprevention of Cancer", "Carcinogenesis", Mar. 2000, pp. 525-530, vol. 21, No. 3.

SEQUENCE LISTING

```
<160> NUMBER OF SEQ ID NOS: 7

<210> SEQ ID NO 1
<211> LENGTH: 14
<212> TYPE: PRT
<213> ORGANISM: Artificial Sequence
<220> FEATURE:
<223> OTHER INFORMATION: VPTD

<400> SEQUENCE: 1

Val Ser Arg Arg Arg Arg Arg Gly Gly Arg Arg Arg Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: HPTD

<400> SEQUENCE: 2

Cys Ser Ser Arg Lys Lys Asn Pro Asn Cys Arg Arg His
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Penetratin

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: polyarginine

<400> SEQUENCE: 4

Arg Arg Arg Arg Arg Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: polylysine

<400> SEQUENCE: 5

Lys Lys Lys Lys Lys Lys Lys Lys Lys Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: defensin

<400> SEQUENCE: 6

Gly Lys Cys Ser Thr Arg Gly Arg Lys Cys Cys Arg Arg Lys Lys
1               5                   10                  15
```

```
<210> SEQ ID NO 7
<211> LENGTH: 11
<212> TYPE: PRT
<213> ORGANISM: Artificial Sequence
<220> FEATURE:
<223> OTHER INFORMATION: Human immunodeficiency virus-1

<400> SEQUENCE: 7

Tyr Gly Arg Lys Lys Arg Arg Gln Arg Arg Arg
1               5                   10
```

PEPTIDE HAVING CANCER SELECTIVE TRANSLOCATION FUNCTION AND USE THEREOF

CROSS-REFERENCE TO RELATED APPLICATIONS

This is a continuation under 35 USC 119 of U.S. patent application Ser. No. 14/395,807 filed Oct. 20, 2014 for PEPTIDE HAVING CANCER SELECTIVE TRANSLOCATION FUNCTION AND USE THEREOF, which in turn is a U.S. national phase under the provisions of 35 U.S.C. §371 of International Patent Application No. PCT/KR13/08324 filed Sep. 16, 2013, which in turn claims priority of Korean Patent Application No. 10-2012-0103620 filed Sep. 18, 2012. The disclosures of all such patent applications are hereby incorporated herein by reference in their respective entireties, for all purposes.

TECHNICAL FIELD

The present invention relates to a peptide having cancer selective translocation function, and the use thereof, and more particularly to a peptide having cancer selective translocation function, a conjugate comprising a drug such as an anticancer agent linked to the peptide having cancer selective translocation function, and the use thereof.

The peptide having cancer selective translocation function of the present invention or a conjugate of the peptide and a drug can selectively penetrate tumor cells or tumor tissues, and thus can be widely used for the diagnosis or treatment of various cancers.

BACKGROUND ART

For the treatment of tumors or the diagnosis and treatment of inflammations, for example, osteoarthritis, and skin diseases, many studies have been conducted on proteins or small materials, which are present specifically in disease foci. Thus, many kinds of such materials have been identified while studies on treatment with such materials have also been actively conducted. For example, it was shown that prostate-specific antigen (PSA) is frequently present in prostate cancer, and matrix metalloprotease (MMP) is highly expressed specifically in arthritis tissue or other tumor tissues compared to that in normal tissue. Thus, such materials have been targeted in disease research and treatment. However, if materials that are used for the diagnosis and treatment of diseases do not act specifically against such targets only, problems of side effects and low image quality will be caused by non-specific distribution of the materials. For this reason, there has been a demand for the development of formulations that remain or act specifically in their targets.

Meanwhile, only some small materials can enter the cytoplasm or nucleus of live cells through the cell membrane at a very low ratio, whereas large molecules cannot enter cells. Because most materials prepared for therapeutic, preventive or diagnostic purposes, each of which requires an effective amount to be delivered into cells, are large molecules or macromolecules, methods of delivering biologically active macromolecules into cells without damaging the cells both in vivo and ex vivo have been demanded.

As a result of studies conducted to satisfy this demand, protein transduction domains (PTDs) have been suggested, and among them, TAT protein, which is the transcription factor of human immunodeficiency virus-1 (HIV-1), has been most frequently studied. It was found that the TAT protein is more effective in passing through the cell membrane when it is composed of amino acids 47 to 57 (YGRKKRRQRRR), on which positively charged amino acids are concentrated, compared to when it is in a full-length form consisting of 86 amino acids (Fawell, S. et al., *Proc. Natl. Acad. Sci. USA*, 91:664, 1994). Other examples verifying the effects of PTDs include a peptide having a sequence of amino acids 267 to 300 of the VP22 protein of Herpes Simplex Virus type 1 (HSV-1) (Elliott, G. et al., Cell, 88:223, 1997), a peptide having a sequence of amino acids 84 to 92 of the UL-56 protein of HSV-2 (GeneBank code: D1047[gi:221784]), and a peptide having a sequence of amino acids 339 to 355 of the Antennapedia (ANTP) protein of *Drosophila* sp (Schwarze, S. R. et al., *Trends. Pharmacol. Sci.*, 21:45, 2000). In addition, artificial peptides consisting of positively charged amino acids also showed the effect of delivering drugs (Laus, R. et al., *Nature. Biotechnol.*, 18:1269, 2000).

Recently, the present inventors reported the preparation of a low-molecular-weight protamine (LMWP) and the cell-penetrating activity thereof, in which the low-molecular-weight protamine (LMWP) has a peptide sequence similar to TAT, serves as a protein transduction domain and contains a large amount of cationic amino acids such as arginine. Particularly, the LMWP peptide is a naturally occurring cationic peptide from protamine and is advantageous in that it presents no toxicity concerns and can be produced in large amounts (Park, Y. J. et al., *J. Gene. Med.*, 700, 2003). Meanwhile, the present inventors have found that the LMWP peptide selectively binds to vascular endothelial growth factor (VEGF) and heparin, which are distributed specifically in tumor tissue, and have expected that the peptide would have the effect of selectively inhibiting tumors. Meanwhile, this LMWP peptide will hereinafter be referred to as "VEGF-binding protein transduction domain (VPTD) or peptide".

The present inventors have found that a VEGF-binding protein transduction domain (VPTD) peptide represented as SEQ ID NO: 1 or a heparin-binding protein transduction domain (HPTD) peptide represented as SEQ ID NO: 2 binds specifically to vascular endothelial growth factor (VEGF) and heparin in tumor cells or tumor tissues and also accumulates selectively in tumor cells or tumor tissues to inhibit the growth of the tumor cells, thereby completing the present invention.

DISCLOSURE OF INVENTION

It is an object of the present invention to provide a peptide which can minimize problems associated with side effects or low image quality, which can occur due to the non-specific distribution of conventional tumor diagnostic or therapeutic agents, in which the peptide can deliver tumor diagnostic agents or disease therapeutic agents selectively to target cells only.

Accordingly, a main object of the present invention is to reconstitute the oxidation/reduction balance in mutant strains, which lack each of 472 genes involved in breathing, electron transfer and oxidation/reduction reactions, at the genome-wide level by anaerobic fermentation, and based on the reconstitution, select genes capable of controlling the carbon metabolic flow and provide a mutant microorganism in which lactic acid, succinic acid or ethanol is produced in large amounts but the production of other organic acids is significantly reduced, and a method for producing the mutant microorganism. Still another object of the present invention is to use the peptide for the diagnosis or treatment of cancer.

BRIEF DESCRIPTION OF THE DRAWINGS

FIG. 1A is a graphic diagram showing the results of flow cytometry, and FIG. 1B is a set of confocal scanning microscope images showing the observation of the results shown in FIG. 1A.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

The definition of major terms used in the present invention is as follows.

As used herein, the term "protein transduction domain (PTD)" refers to a cell-penetrating peptide capable of delivering drugs or drug-containing particles into the cytoplasm or nucleus of cells. Specifically, the term refers to a peptide that can form a covalent bond with oligonucleotides, peptides, proteins, oligosaccharides, polysaccharides or nanoparticles to introduce these materials into cells without needing to use a separate receptor, carrier or energy. The inventive VEGF-binding protein transduction domain peptide represented as SEQ ID NO: 1 and the inventive heparin-binding protein transduction domain peptide represented as SEQ ID NO: 2 are also included in the scope of the PTD.

As used herein, the term "tumor cell" or "tumor tissue" refers to an in vivo or ex vivo cell or tissue into which a drug or a drug-containing particle are delivered by a tumor-penetrating peptide. In other words, as used herein, the term "tumor tissue" is meant to include in vivo cells, that is, cells that constitute the organ or tissue of living animals or humans, or microorganisms that are found in living animals or humans.

In one aspect, the present invention provides peptide having cancer selective translocation function comprising VPTD (VEGF-binding protein transduction domain peptide) peptide represented as SEQ ID NO: 1 or HPTD (heparin-binding protein transduction domain) peptide represented as SEQ ID NO: 2, and a composition for enhancing cancer selective translocation, which comprises the peptide as an active ingredient.

Figure 2:
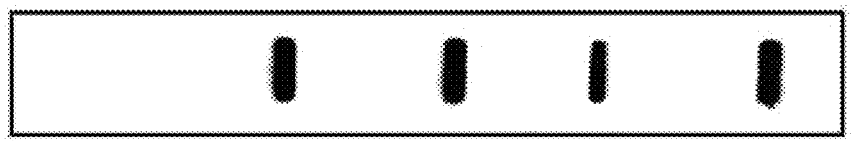
FIG. 2 shows the results of examining the accuracy of synthesis of the inventive VPTD peptide represented as SEQ ID NO: 1 or the inventive HPTD peptide represented as SEQ ID NO: 2 and measuring the binding affinity between the peptides and their targets, VEGF and heparin.
Figure 2:
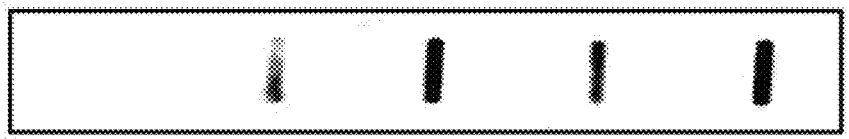
Figure 2:
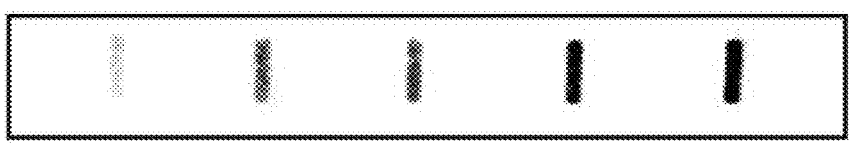
Figure 2:
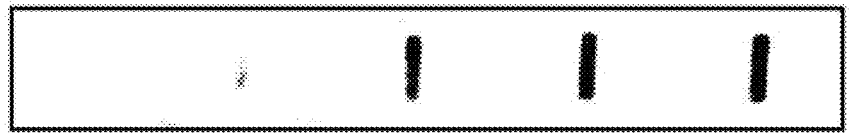

The VPTD peptide represented as SEQ ID NO: 1 or the HPTD peptide represented as SEQ ID NO: 2 is characterized in that it binds specifically to vascular endothelial growth factor (VEGF) and heparin in tumor cells or tumor tissue (see FIG. 2). The expression level of VEGF or heparin in tumor cells or tumor tissue is higher than that in normal tissue, and thus the inventive peptide represented as SEQ ID NO: 1 or 2 can bind specifically to tumor tissue or tumor cells. Also, the VPTD peptide represented as SEQ ID NO: 1 or the VPTD peptide represented as SEQ ID NO: 2, according to the present invention, has the ability to penetrate cells, and thus can bind specifically to VEGF or heparin, and then enter cells without having to use endocytosis that is a conventional intracellular absorption process. Thus, it can accumulate selectively in tumor cells or tumor tissue.

The VPTD peptide represented as SEQ ID NO: 1 or the VPTD peptide represented as SEQ ID NO: 2 may be composed of D-type or L-type amino acids depending on in vivo stability and may contain one or more amino acids selected from the group consisting of arginine, lysine and histidine in an amount of 70-80%.

Examples of protein transduction domains (PTDs) having the above-described characteristic include, in addition to the protein transduction domains VPTD (SEQ ID NO: 1; VSRRRRRRGGRRRR) and HPTD (SEQ ID NO: 2; CSSRKKNPNCRRH) found by the present inventors, cationic protein transduction domains having an arginine, lysine or histidine content of 70-80% or more, such as penetratin (SEQ ID NO: 3; RQIKIWFQNRRMKWKK), polyarginine (SEQ ID NO: 4; RRRRRRR), polylysine (SEQ ID NO: 5; KKKKKKKKKK), a protamine fragment, and Antennapedia (ANTP), as well as defensin-derived HBD (SEQ ID NO: 6:GKCSTRGRKCCRRKK) and TAT (SEQ ID NO: 7: YGRKKRRQRRR). Thus, the PTDs of SEQ ID NO: 3 to SEQ ID NO: 7 may also be used as a substitute for the peptide of SEQ ID NO: 1 or 2.

In another aspect, the present invention provides a method of using the VPTD peptide of SEQ ID NO: 1 or the HPTD peptide of SEQ ID NO: 2 to diagnose or treat cancer.

The VPTD peptide of SEQ ID NO: 1 or the HPTD peptide of SEQ ID NO: 2 binds specifically to vascular endothelial growth factor (VEGF) and heparin in tumor cells or tumor tissue and accumulates in the tumor cells or tumor tissue, and thus the peptide can be used for the diagnosis or treatment of cancer.

In still another aspect, the present invention provides contrast agent for cancer diagnosis having cancer selective translocation function, which comprises VPTD peptide represented as SEQ ID NO: 1 or HPTD peptide represented as SEQ ID NO: 2 to which a fluorescent substance is bound.

Figure 1A:
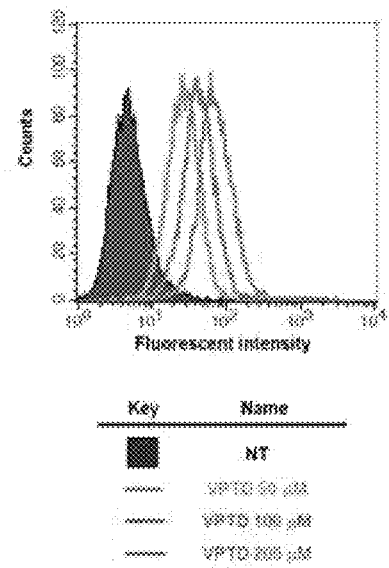
FIGS. 1A and 1B show the results of measuring the tumor cell-penetrating abilities of a VEGF-binding protein transduction domain (VPTD) peptide represented as SEQ ID NO: 1 (VSRRRRRRGGRRRR) and a heparin-binding protein transduction domain (HPTD) represented as SEQ ID NO: 2. Specifically.
Figure 1A:
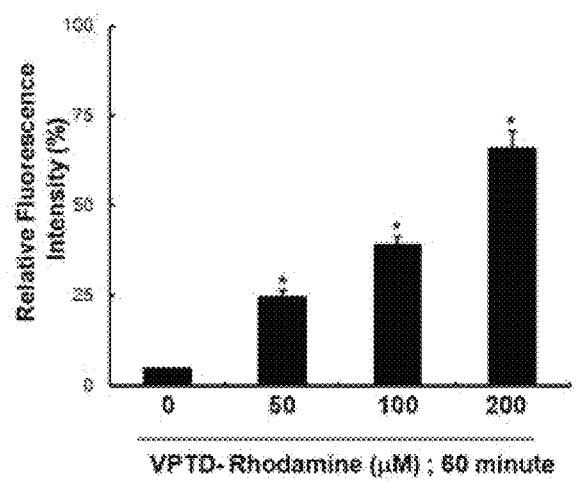
Figure 1A:
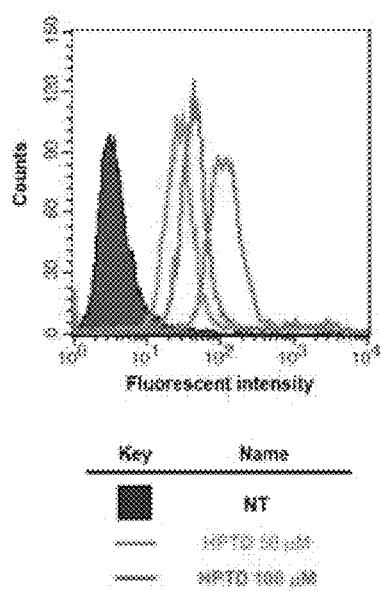
Figure 1A:
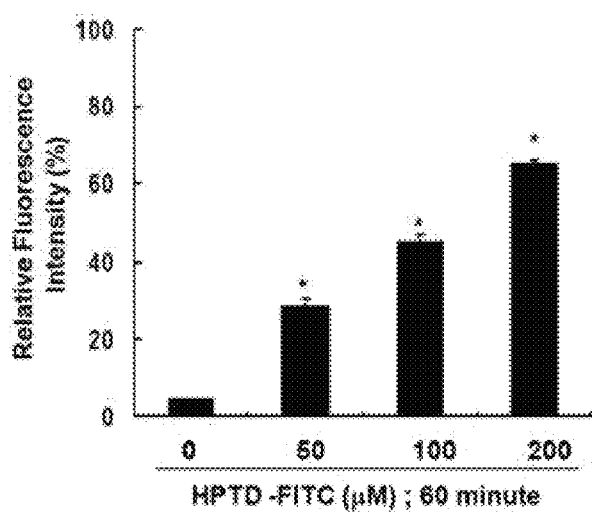
Figure 1B:
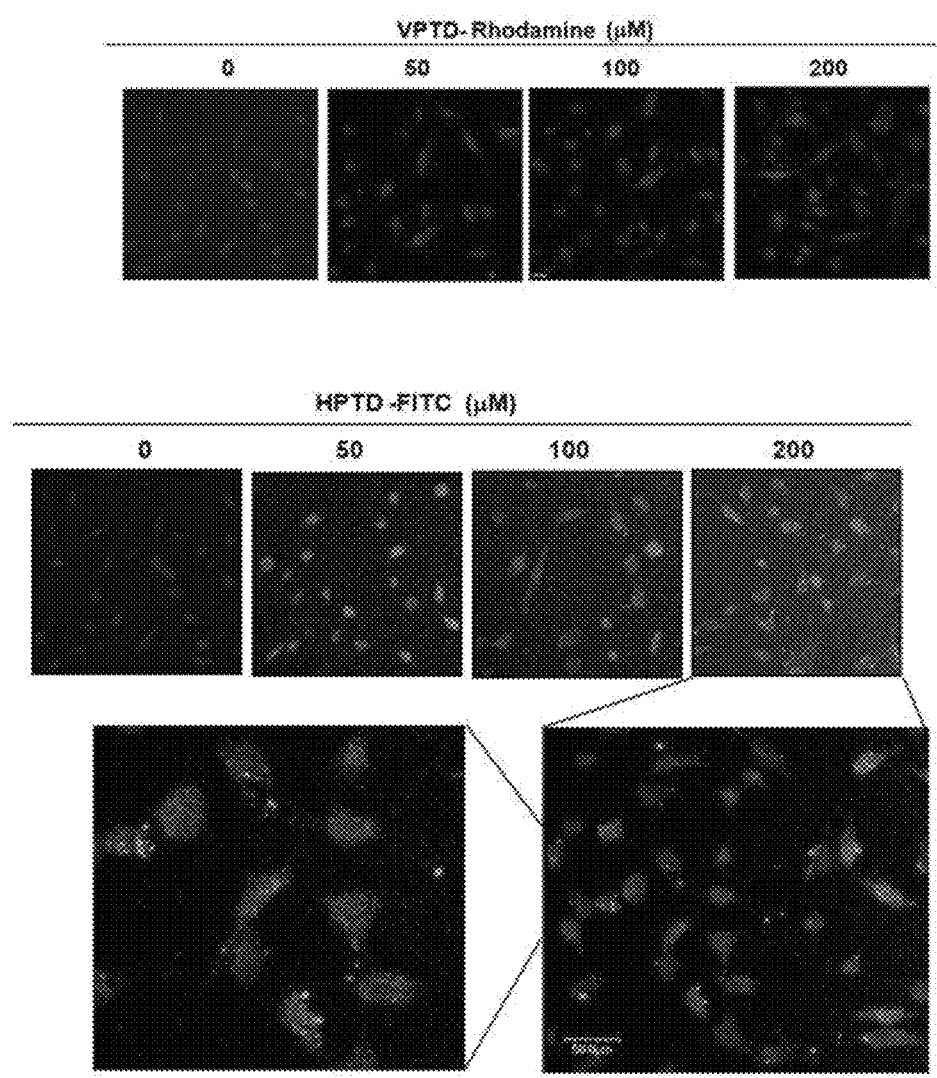

Because the VPTD peptide represented as SEQ ID NO: 1 or the HPTD peptide represented as SEQ ID NO: 2 accumulates selectively in tumor cells or tumor tissues, a conjugate comprising a fluorescent substance bound to the peptide may be used as a contrast agent for cancer diagnosis (see Example 3 and FIGS. 1A and 1B).

The fluorescent substance that is used in the present invention may be selected from the group consisting of fluorescein isothiocyanate (FITC), radioisotopes, quantum dots, MRI contrast agents, fluorescein, tetramethylrhodamine, BODIPY, and Alexa, but is not limited thereto.

In yet another aspect, the present invention provides a composition for treating cancer having cancer selective translocation function, which comprises VPTD peptide represented as SEQ ID NO: 1 or HPTD peptide represented as SEQ ID NO: 2.

Because the VPTD peptide represented as SEQ ID NO: 1 or the HPTD peptide represented as SEQ ID NO: 2 according to the present invention shows the effect of inhibiting the growth of tumor cells by its selective binding to VEGF and heparin, which are highly expressed in tumor cells or tumor tissue (see Examples 4 and FIGS. 2 and 3), the composition containing the peptide may also be used as a composition for treating cancer.

In a further aspect, the present invention provide a peptide having cancer selective translocation function-drug conjugate, which comprises a drug chemically linked to the N-terminus or C-terminus of VPTD peptide represented as SEQ ID NO: 1 or HPTD peptide represented as SEQ ID NO: 2.

The VPTD peptide represented as SEQ ID NO: 1 or the HPTD peptide represented as SEQ ID NO: 2 and the drug may be linked to each other by a cysteine. Specifically, the peptide-drug conjugate is prepared by linking a drug having a thiol group to the N-terminus or C-terminus of the peptide of SEQ ID NO: 1 or 2, which contains a cysteine. If the above-described peptide analogue is used as a substitute for the peptide of SEQ ID NO: 1 or 2, the peptide-drug conjugate may also be prepared by attaching a cysteine to the terminus of the peptide, and then reacting the peptide with a drug. Examples of the drug having a thiol group include not only drugs that naturally contain a thiol group, but also drugs modified to have a thiol group.

In addition, the peptide-drug conjugate may also be prepared by linking the peptide with the drug by a cross-linking agent. Because the N-terminus of the protein transduction domain (PTD) peptide has a free amino group, it is easy to form the peptide-drug conjugate by a crosslinking agent. Examples of the crosslinking agent that can be used in the present invention include, but not limited to, 1,4-bis-maleimidobutane (BMB), 1,11-bis-maleimidotetraethyleneglycol (BM[PEO]4), 1-ethyl-3-[3-dimethyl aminopropyl] carbodiimide hydrochloride (EDC), succinimidyl-4-[N-maleimidomethylcyclohexane-1-carboxy-[6-amidocaproate]] (SMCC) and its sulfonate (sulfo-SMCC), succimidyl 6-[3-(2-pyridyldithio)-ropionamido] hexanoate (SPDP) and its sulfonate (sulfo-SPDP), m-maleimidobenzoyl-N-hydroxysuccinimide ester (MBS) and its sulfonate (sulfo-MBS), and succinimidyl[4-(p-maleimidophenyl) butyrate] (SMPB) and its sulfonate (sulfo-SMPB). If the cell-penetrating peptide and a drug or a drug-containing nanoparticle are linked to each other by an S—S bond, the drug can be dissociated from the cell-penetrating peptide by reductase or the like in cells. If this method is used, drugs, proteins or other nanoparticles can be introduced into cells in an easy and convenient manner without having to use a recombinant vector that is constructed in a time-consuming manner, and thus the desired therapeutic can be easily achieved.

Examples of the drug that is used in the present invention include anticancer agents, anti-inflammatory agents, bone resorption inhibitors, anticancer proteins, anti-inflammatory proteins, immune-enhancing proteins, anticancer and anti-inflammatory siRNAs, oligonucleotides, and magnetic nanoparticles containing them. As used herein, the term "siRNA" refers to RNA that silences the expression of the target RNA. The target RNA is the mRNA transcribed from a gene that causes disease, particularly a tumor or inflammation. Examples of oncogenes include, but are not limited to, vascular endothelial growth factor (VEGF) gene.

The aforementioned protein that causes a tumor or inflammatory disease may be selected from the group consisting of vascular endothelial growth factor (VEGF), B-cell leukemia/lymphoma 2 (BCL2), epidermal growth factor receptor (EGFR), human epidermal growth factor receptor 2 (HER2), Janus kinase (JAN), and phosphatidylinositol-3-kinase/Akt kinase (PI3-K/AKT).

In a still further aspect, the present invention provides a drug delivery system having cancer selective translocation function, which comprises a drug linked to the N-terminus or C-terminus of VPTD peptide represented as SEQ ID NO: 1 or HPTD peptide represented as SEQ ID NO: 2.

In a yet further aspect, the present invention provides a composition for treating cancer comprising a peptide having cancer selective translocation function-drug conjugate, which comprises a drug chemically linked to the N-terminus or C-terminus of VPTD peptide represented as SEQ ID NO: 1 or HPTD peptide represented as SEQ ID NO: 2.

The composition for treating cancer according to the present invention can be administered with a pharmaceutically acceptable carrier. For example, for oral administration, the composition of the present invention can comprise binders, lubricants, disintegrants, excipients, emulsifiers, dispersions, stabilizers, suspending agents, pigments, perfumes, etc., for injection administration, the composition can comprises buffers, preservatives, analgesics, emulsifiers, isotonic agents, stabilizers, etc., and for local administration, the composition can comprises bases, excipients, lubricants, preservatives, etc.

The inventive composition for treating cancer can be formulated with a pharmaceutically acceptable carrier as described above in various manners. For example, for oral administration, the composition of the present invention can be formulated in the form of tablet, troche, capsule, elixir, suspension, syrup, wafer, etc., and for injection administration, the composition can be formulated as a unit dosage ampoule or a multiple dosage form.

The inventive composition for treating cancer can be administered in an effective amount for the therapeutic or prevention purpose. The dose of the composition of the present invention may vary depending on various factors, such as disease type and severity, age, sex, body weight, sensitivity to drugs, type of current therapy, mode of administration, target cell, etc., and may be easily determined by those of ordinary skill in the art. The composition of the present invention may also be administered in combination with conventional therapeutic or preventive agents for cancer, sequentially or simultaneously with the conventional therapeutic agents, and in single dose or multiple doses. Preferably, with all of the factors taken into account, it is imperative that the minimum dose required to achieve the maximum effect without side effects be administered, which can be easily determined by those of ordinary skill in the art. As used herein, the term "administration" means introducing a desired material into a patient by any suitable method. The pharmaceutical composition of the present invention may be administered through any general route, as long as it can reach a desired tissue. The composition of the present invention can be administered intraperitoneally, intravenously, intramuscularly, subcutaneously, transdermally, orally, topically, intranasally, intrapulmonarily or intrarectally, but is not limited thereto. In addition, the pharmaceutical composition of the present invention may also be administered by any device that can deliver the active ingredient into target cells.

Particularly, although the following examples illustrated only the anticancer protein Gelonin as a drug, it will be obvious to those skilled in the art that the use of other anticancer proteins, an antisense oligonucleotide against an oncogene, an siRNA, or particles containing them, can also show tumor therapeutic effects that are equal or similar to those of the use of Gelonin, and that the use of an anti-inflammatory agent or an anti-inflammatory protein as a drug can also show anti-inflammatory effects.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Preparation of Target-Selective Cell/Tissue-Penetrating Peptide

Peptides were prepared by the F-moc chemistry method using an automatic peptide synthesizer, and then the peptide moieties were cut by resin, washed, freeze-dried, followed by purification by liquid chromatography, thereby preparing a VPTD peptide represented as SEQ ID NO: 1 (VSRRRRRRGGRRRR) and an HPTD peptide represented as SEQ ID NO: 2 (CSSRKKNPNCRRH). The molecular weights of the purified peptides were analyzed by MALDI.

Example 2: Preparation of Tumor-Targeting and Tumor-Penetrating Peptide-Drug Conjugates The VPTD peptide of SEQ ID NO: 1 and the HPTD peptide of SEQ ID NO: 2, prepared in Example 1, contained the free-sulfhydryl group of a cysteine residue, and thus chemical linkage between the peptide and the anticancer protein RNase or doxorubicin was induced using the free-sulfhydryl group as a chemical crosslinking agent. The surfaces of RNase and doxorubicin (Dox) were modified to have a thiol group attached to the carboxyl group on the surfaces. 10 molecules of peptide-SH were added to 1 molecule of particle surface-SH and reacted at 4° C. for 12 hours, and then unreacted molecules were removed by ultrafiltration, followed by freeze drying, thereby obtaining a conjugate of the VPTD peptide of SEQ ID NO: 1 and RNase, a conjugate of the VPTD peptide of SEQ ID NO: 1 and Dox, a conjugate of the HPTD peptide of SEQ ID NO: 2 and RNase, and a conjugate of the HPTD peptide of SEQ ID NO: 2 and Dox.

Example 3: Tumor Cell Penetration Abilities of Tumor-Targeting and Cell-Penetrating Peptides In order to test the tumor cell-targeting and tumor cell-penetrating abilities of the VPTD peptide of SEQ ID NO: 1 and the HPTD peptide of SEQ ID NO: 1, prepared in Example 1, the termini of the prepared peptides were labeled with a fluorescent dye, and then each of the peptides was inoculated into a tumor cell line (MDA-MB-231, ATCC) at various concentrations.

60 minutes after the inoculation, the fluorescence of the cells was measured by FACS, and the results of the measurement are shown in FIGS. 1A and 1B. As can be seen in FIG. 1A, the fluorescence of the tumor cells increased in a manner dependent on the concentration of the peptide. FIG. 1B shows the results of observing the fluorescence of the tumor cells by a confocal laser scanning microscope in order to examine the tumor cell penetration abilities of the VPTD peptide of SEQ ID NO: 1 and the HPTD peptide of SEQ ID NO: 1. In FIG. 1B, in order to demonstrate that the stained portion is the cells, the cell nuclei were stained with Hoechst 33342 (5 µg/ml), and then the cells were fixed with 10% neutral formalin solution. As a result, as can be seen in FIG. 1B, the abilities of the peptide to penetrate the tumor cell line increased in a manner dependent on the concentration of the peptide.

Example 4: Measurement of Tumor Inhibitory Effects of Tumor-Targeting and Target-Penetrating Peptide-Anticancer Agent Conjugates In order to test the effects of the VPTD peptide of SEQ ID NO: 1 (VSRRRRRRGGRRRR) and the HPTD peptide of SEQ ID NO: (CSSRKKNPNCRRH), prepared in Example 1, and the tumor-targeting and tumor-penetrating peptide-drug conjugates prepared in Example 2, a tumor was induced in mice, and when the tumor grew to a predetermined size, each of the peptides prepared in Example 1 and the tumor-targeting and tumor-penetrating peptide-drug conjugates prepared in Example 2 was injected into the mice. After injection, the volume of the tumor was measured at intervals of 3-4 days for 30 days. On day 30, the mice were sacrificed, and the tumor was extracted and photographed.

Figure 3:
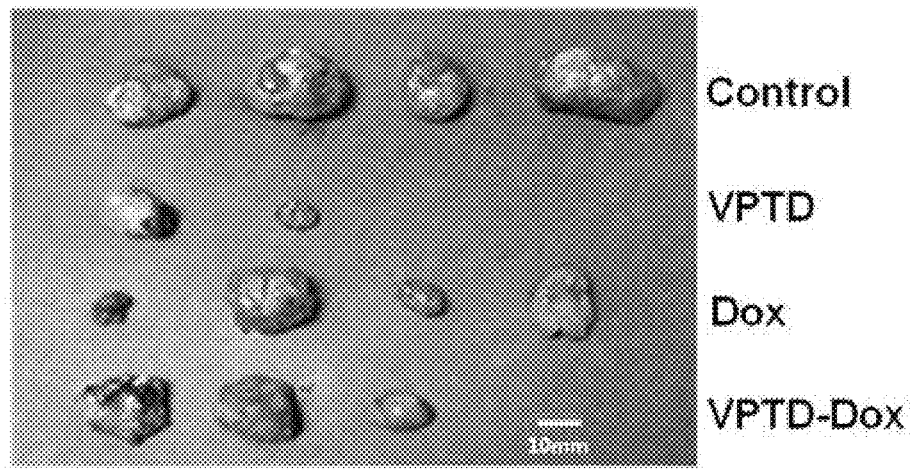
FIG. 3 shows the results of examining the tumor inhibitory effects of the inventive VPTD peptide represented as SEQ ID NO: 1, an anticancer agent (Dox; doxrubicin), and a conjugate of the VPTD peptide of SEQ ID NO: 1 and the anticancer agent (Dox).
Figure 3:
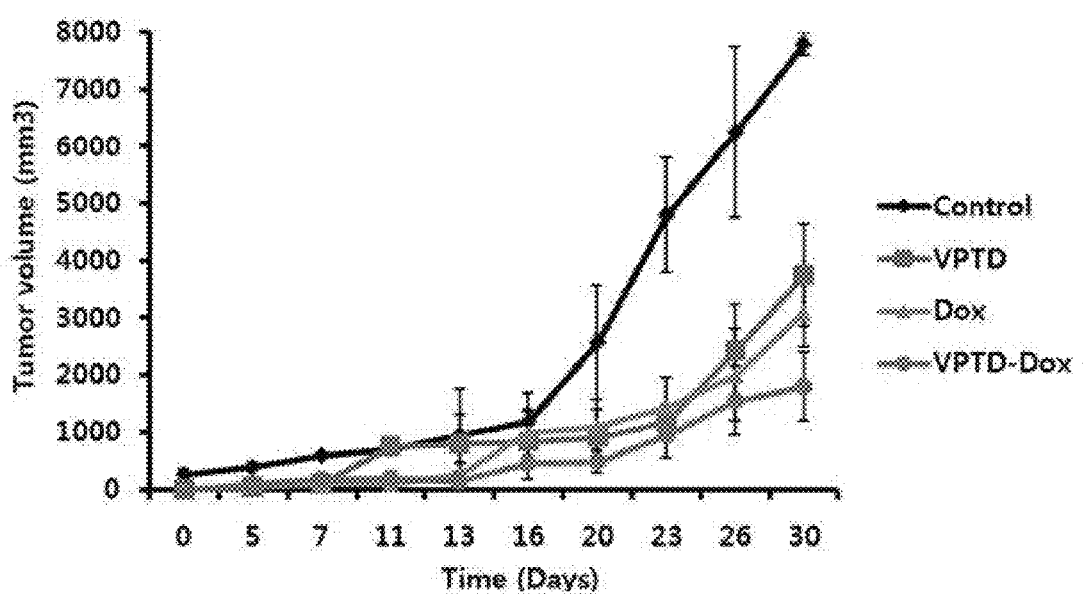

As a result, as shown in FIG. 3, in the tumor-induced mice treated with a control, the tumor was not inhibited, whereas in the tumor-induced mice treated with each of the VPTD peptide and the VPTD peptide-drug (Dox) conjugate, the progression of the tumor was significantly inhibited. This is believed to be because the tumor-penetrating ability of the VPTD peptide of the present invention was maximized in the tumor tissue and the VPTD peptide did bind specifically to VEGF to inhibit vascular formation essential for the formation and progression of tumors. To demonstrate such results, the ability of the inventive VPTD peptide of SEQ ID NO: 1 or the inventive HPTD peptide of SEQ ID NO: 2 to bind to VEGF and heparin was evaluated by slot-blot analysis. As a result, it could be seen that the VPTD peptide and the HPTD peptide did all bind to VEGF and heparin, which are overexpressed in tumor cells or tumor tissue.

As described above, the tumor-targeting and tumor-penetrating peptide of the present invention and a conjugate of the peptide and a drug break from conventional non-specific and non-selective transduction peptides, and can maximize the effects of diagnosis and drug therapies through optimal targeting, and the side effects thereof in the body can be minimized. Thus, the use of the tumor-selective and tumor-penetrating peptide according to the present invention can present innovative disease diagnostic and therapeutic technologies.

INDUSTRIAL APPLICABILITY

As described above, the peptide or peptide-drug conjugate of the present invention selectively penetrates tumor cells or tumor tissue only, and thus can be used for the diagnosis or treatment of cancer. Conventional drugs or materials that are used in the diagnosis or treatment of tumors can cause unexpected side effects if they are distributed non-specifically in vivo, and in many cases, it is difficult to achieve accurate diagnosis using the conventional drugs or materials. However, the use of the peptide of the present invention can solve such problems.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of treating a breast cancer, said method comprising a step of administering a peptide having cancer selective translocation function-doxorubicin conjugate, which comprises doxorubicin chemically linked to the N-terminus or C-terminus of VEGF-binding protein transduction domain (VPTD) peptide represented as SEQ ID NO: 1, wherein the VPTD peptide represented as SEQ ID NO: 1 and doxorubicin are linked to each other by a disulfide bond, and wherein the VPTD peptide represented as SEQ ID NO: 1 binds specifically to vascular endothelial growth factor (VEGF) in tumor cells or tumor tissues.

2. The method of claim 1, wherein doxorubicin and the VPTD peptide are chemically linked by any one crosslinking agent selected from the group consisting of 1,4-bis-maleimidobutane (BMB), 1,11-bis-maleimidotetraethyleneglycol (BM[PEO]4), 1-ethyl-3-[3-dimethyl aminopropyl] carbodiimide hydrochloride (EDC), succinimidyl-4[N-maleimidomethylcyclohexane-1-carboxy-[6 amidocaproate]] (SMCC) and its sulfonate (sulfo-SMCC), succimidyl 6-[3-(2-pyridyldithio) ropionamido] hexanoate (SPDP) and its sulfonate (sulfo-SPDP), m-maleimidobenzoyl-Nhydroxysuccinimide ester (MBS) and its sulfonate (sulfo-MBS), and succimidyl[4-(pmaleimidophenyl) butyrate] (SMPB) and its sulfonate (sulfo-SMPB).

* * * * *

UNITED STATES PATENT AND TRADEMARK OFFICE
CERTIFICATE OF CORRECTION

PATENT NO. : 9,849,190 B2  
APPLICATION NO. : 15/234396  
DATED : December 26, 2017  
INVENTOR(S) : Yoon Jeong Park et al.

Page 1 of 1

It is certified that error appears in the above-identified patent and that said Letters Patent is hereby corrected as shown below:

In the Specification

Column 7, Line 2: "a gent or an anti-inflammatory protein" should be --agent or an anti-inflammatory protein--.

Column 8, Line 12: "SEQ ID NO: (CSSRKKNPNCRRH)" should be --SEQ ID NO: 2 (CSSRKKNPNCRRH)--.

Signed and Sealed this  
Twenty-ninth Day of May, 2018

Andrei Iancu  
*Director of the United States Patent and Trademark Office*